United States Patent [19]
Kassis et al.

[11] Patent Number: 5,574,148
[45] Date of Patent: Nov. 12, 1996

[54] RAPID SYNTHESIS OF RADIOLABELED PYRIMIDINE NUCLEOSIDES OR NUCLEOTIDES

[75] Inventors: Amin I. Kassis, Chestnut Hill; Catherine F. Foulon, Brookline; S. James Adelstein, Waban, all of Mass.

[73] Assignee: President U Fellows of Harvard College, Cambridge, Mass.

[21] Appl. No.: 382,892

[22] Filed: Feb. 2, 1995

[51] Int. Cl.$^6$ ............... C07H 19/067; C07H 19/073
[52] U.S. Cl. ............... 536/28.52; 536/28.55; 536/124
[58] Field of Search ............... 536/28.52, 28.55, 536/124; 514/49, 50

[56] References Cited

U.S. PATENT DOCUMENTS

| | | | |
|---|---|---|---|
| 4,851,520 | 7/1989 | Kassis et al. | 536/26.14 |
| 5,077,034 | 12/1991 | Kassis et al. | 424/1.73 |
| 5,094,835 | 3/1992 | Kassis et al. | 424/1.73 |
| 5,308,605 | 5/1994 | Kassis et al. | 424/1.73 |

FOREIGN PATENT DOCUMENTS 8907106  8/1989  WIPO.

OTHER PUBLICATIONS

Baranowska–Kortylewicz et al.(I), "Radiolabeling Kit/Generator for 5–Radiohalogenated Uridines", *J. Labelled Cmpds. Radiopharmaceuticals*, 34(6), 513–521 (1994).

Scherberg, "The Preparation of [$^{125}$I]Iododeoxyuridine–labeled Oligomers by Automated Synthesis with an $^{125}$I–Nucleoside Phosphoramidite," *Applied Radiation and Isotopes*, 44(4), 665–671 (1993).

Scherberg et al., "Preparation of 125I–2'–Deoxyuridine Triphosphate and Incorporation of the Labeled Nucleotide into DNA by the Polymerase Chain Reaction," *Bioorg. Khim.*, 18(8), 1104–1107 (1992).

Mease et al. "Synthesis of High Specific Activity $^{80m}$Br and $^{123}$I Labeled 5–Halodeoxyuridines and Other $^{80m}$Br Compounds for the Study of Auger Electron Toxicity," *J. Labelled Cmpds. Radiopharmaceuticals*, 29(4), 393–403 (1991).

Meunier et al., "Synthèse, Caractèrisation et Propriètès Cytoxiques des Premiers Metallocènonuclèosides", *Eur. J. Medicinal Chem.*, 26, 351–362 (1991).

Baranowska–Kortylewicz et al.(II), "Radioiododemercuration: A Simple Synthesis of 5–[$^{123/125/127}$I]iodo–2'–deoxyuridine," *Applied Radiation and Isotopes*, 39(4), 335–341 (1988); *Chem. Abstr.*, 109(5), p. 653, Abstract No. 38175t, 1988; only Abstract provided.

Reefschläger et al., "Synthesis and Biological Activities of 4–O–(Difluoromethyl)–5–Substituted–Uracil Nucleoside Analogues," *J. Medicinal Chem.*, 31(2), 393–397 (1988).

Khamis et al., "Investigation of Complexes Formed Between Gene 32 Protein from Bacteriophage T4 and Heavy–Atom–Modified Single–Stranded Polynucleotides Using Optical Detection of Magnetic Resonance," *Biochemistry*, 25(20), 5865–5872 (1986).

Visser et al., "The Preparation of Aromatic Astatine Compounds Through Aromatic Mercury Compounds. Part II. Astatination of Pyrimidines and Steroids," *J. Labelled Cmpds. Radiopharmaceuticals*, 18(6), 799–807 (1981).

Lin et al., "Synthesis and Antiviral Activity of 5–and 5'–Substituted Thymidine Analogs," *J. Medicinal Chem.*, 19(4), 495–498 (1976).

Ötoös et al., "Study of the Synthesis of 5–Alkyl and 5–Halogen Substituted 2–Deoxyuridines," in *Third Symposium on the Chemistry of Nucleic Acid Components, Nucleic Acid Symposium Series No. 1*, A. Williamson ed., Information Retrieval Limited, Washington, D.C., 1975, pp. s49–s52.

*Primary Examiner*—Douglas W. Robinson
*Assistant Examiner*—L. Eric Crane
*Attorney, Agent, or Firm*—George W. Neuner; Sewall P. Bronstein

[57] ABSTRACT

A method of making a radiolabeled pyrimidine nucleoside or nucleotide is described. In the method an aqueous solution (i) a radioactive iodide, bromide, chlorine or astatide ion and (ii) a water soluble halomercuri pyrimidine nucleoside or nucleotide is contacted with an oxidizing agent, whereby a water soluble pyrimidine nucleoside or nucleotide labeled with radioactive iodine, bromide, chlorine or astatine is formed. Kits suitable for practicing the method are also disclosed.

45 Claims, 4 Drawing Sheets

RAPID SYNTHESIS OF RADIOLABELED PYRIMIDINE NUCLEOSIDES OR NUCLEOTIDES

This invention was supported by NIH Grant No. CA 15523 and the government has certain rights to the invention.

FIELD OF INVENTION

This invention relates to methods for making radiolabeled pyrimidine nucleosides and nucleotides and, more specifically, to a fast method for labeling with radioactive iodine, bromine or astatine, particularly by demercurization of a chloromercury precursor.

BACKGROUND OF THE INVENTION

Radiohalogenated pyrimidine nucleosides have been shown to be useful in the diagnosis and treatment of tumors in mammals. For instance, a method of diagnosing tumors using radiohalogenated pyrimidine nucleosides, such as 5-($^{123}$I)Iodo-2'deoxyuridine is described in U.S. Pat. No. 5,094,835 and U.S. Pat. No. 5,308,605, the disclosures of which are incorporated herein by reference. Such radiolabeled compounds can be used to follow the development of tumors. Additionally, tumors in mammals can be treated by injecting or infusing an effective amount of radiohalogenated pyrimidine nucleosides directly to the affected site (see U.S. Pat. No. 5,077,034, the disclosure of which is incorporated herein by reference).

5'-Iodo-2'-deoxyuridine (IUdR) is a thymidine (TdR) analog in which the 5-methyl group of TdR is replaced by iodine. Because the 5-methyl group and the iodine atom have similar van der Waals' radii, this substitution gives a compound that behaves remarkably like TdR and, thus, has been extensively studied. Within the cell, both TdR and IUdR are phosphorylated in a stepwise fashion and are incorporated into DNA. Previous studies have shown that this halogenated nucleotide sensitizes mammalian cells to the effects of radiation. When labeled with the Auger electron emitter $^{123}$I or $^{125}$I, radioiodinated IUdR exhibits substantial toxicity in mammalian cells in vitro (Hofer, K. G., et al., (1975) *Int. J. Radiat. Biol.* 28: 225–241; Chan, P. C., et al., (1976) *Radiat. Res.* 67: 332–343; Kassis, A. I., et al., (1987) *Radiat. Res.* 111: 305–318; Makrigiorgos, G. M., et al., (1989) *Radiat. Res.* 118: 532–544) and is highly therapeutic in several animal tumor models (Bloomer, W. D. and Adelstein, S. J. (1977) *Nature* 265: 620–621; Baranowska-Kortylewicz, J., et al., (1991) *Int. J. Radiat. Oncol. Biol. Phys.* 21: 1541–1551; Kassis, A. I., et al., (1993) *J. Nucl. Med.* 34: 241P). Furthermore, the locoregional (intratumoral, intrathecal, intraperitoneal, intravesical) administration of IUdR radiolabeled with the gamma emitter $^{123}$I or $^{123}$I is useful for scintigraphic detection of animal and human tumors (Kassis, A. I., (1990) *J. Nucl. Med. Allied Sci.* 34: 299–303; Kassis, A. I., (1990) *Cancer Res.* 50: 5199–5203; Baranowska-Kortylewicz, J., et al., (1991) supra; Van den Abbeele, A. D., et al., (1992) in *Biophysical Aspects of Auger Processes,* American Association of Physicists in Medicine Symposium Proceedings No 8 (Edited by Howell R. W., Narra V. R., Sastry K. S. R. and Rao D. V.) pp. 372–395, American Institute of Physics, Woodbury, N.Y.; Mariani, G., et al., (1993) *J. Nucl. Med.* 34: 1175–1183; Kassis, A. I., et al., (1994) *Proc. Am. Assoc. Cancer Res.* 35: 414). In addition, intravenously administered radiolabeled IUdR is used in the detection of actively growing regions within tumors (Tjuvajev, J. G., et al., (1994) *J. Nucl. Med.* 35: 1407–1417).

IUdR has certain characteristics which make radiolabeled IUdR useful for the treatment or diagnosis of tumors whether macroscopically observable or not. For instance, since IUdR is a low-molecular-weight molecule, it diffuses readily within tissues. When radiolabeled with an Auger electron emitter, e.g., $^{123}$I, $^{125}$I, $^{77}$Br, $^{80m}$BR, IUdR is innocuous outside the cell and ineffective at killing cells when within the cytoplasm. It is, for the most part, taken up selectively by dividing cancerous cells located within nondividing cells and is indefinitely retained following DNA incorporation. Nondividing cells will not incorporate IUdR into their DNA and most of the IUdR that is not taken up by cancerous cells will be catabolized/dehalogenated rapidly [$t_{1/2}$ of min] and thus will not incorporate into the DNA of distant noncancerous dividing cells. Furthermore, since it is a small molecule, IUdR will not induce an antibody response and as such will lend itself to repeated injections/continuous infusion.

Previously described methods for synthesizing radiolabeled IUdR used a demercurization reaction from a suspension of 5-chloromercuri-2'-deoxyuridine (ClHgUdR) in water using sodium [$^{123/125/131}$I] iodine and Iodogen as the oxidant. The IUdR is isolated and, then, purified by HPLC (high performance liquid chromatography) due to the presence of contaminants, such as UdR, ClUdR and mercury. The entire process typically takes approximately 6 hours (Kassis and Baranowska-Kortylewicz, U.S. Pat. No. 4,851, 520; Baranowska-Kortylewicz, J., et al., (1988) *Appl. Radiat. Isot.* 39: 335–341).

Recently, the preparation of radiolabeled IUdR by destannylation of 5-trimethylstannyl-2'-deoxyuridine ((CH$_3$)$_3$SnUdR) has also been described (Baranowska-Kortylewicz, J., et al., (1994) *J. Labelled Cmpd. Radiopharm.* 34: 513–521). The stannyl precursor is more stable than the mercurial precursor. The authors also claim in this publication that, as a consequence of the difference in solubility of the stannyl precursor and IUdR in aqueous solution, radiolabeled IUdR can be isolated by elution through a reverse-phase C$_{18}$ cartridge. However, we have been unable to reproduce these reported results. In fact, IUdR cannot be synthesized from (CH$_3$)$_3$SnUdR precursor using the conditions prescribed in this publication. Furthermore, contrary to this publication, IUdR cannot be eluted from reverse planar C-18 adsorbants.

It can be appreciated that it is desirable to have a method for synthetic preparation of radiolabeled pyrimidine nucleosides or nucleotides that is rapid, efficient, and easily reproducible. It is further desirable that such a process produces radiolabeled nucleosides or nucleotides free of toxic contaminants and which therefore do not require further purification.

SUMMARY OF THE INVENTION

The method of this invention comprises the use of a water soluble mercurial precursor of the desired radiolabeled nucleoside or nucleotide to produce a radiolabeled nucleoside or nucleotide. First, a water soluble halomercuri nucleoside or nucleotide compound is prepared from the recrystallized mercuri compound. Applicants have discovered that, although prior mercuri precursor compounds have been insoluble in water, recrystallization of these derivatives following their solubilization by the addition of excess salt, e.g., NaCl, surprisingly can produce precursor compounds having solubility in water, e.g., on the order of 1 mg/ml. Radioactive halide, particularly, iodide, bromide or astatide, is then added to the aqueous suspension of the water soluble, recrystallized halomercuri nucleoside or nucleotide in the presence of an oxidant, for example, Iodogen or $H_2O_2$.

At room temperature, the reaction replacing mercury with radioactive iodine, bromine, or astatine is complete in about 15 seconds when using the water soluble precursor mercury compound. After demercurization, the final radiolabeled nucleoside or nucleotide synthesized from the water soluble halomercuri derivative and contains no UV-absorbing contaminant. Therefore, for example, no-carrier added radioiodinated, radiobrominated or astatinated nucleoside or nucleotide can be easily prepared that is suitable for biological or clinical use.

In one preferred embodiment of the invention, the mercurial precursor is chelated to a cationic exchange resin and, subsequently, radiolabeled (see FIG. 1 illustrating radioiodination). The final radiolabeled nucleoside or nucleotide synthesized from the chelated precursor contains no UV-absorbing contaminants and, therefore, this method allows for the preparation of no-carrier-added, radioiodinated, radiobrominated, or astatinated nucleoside or nucleotide suitable for biological or clinical use. Alternatively, the resin is incubated with the radiolabeled nucleoside or nucleotide containing solution prepared by demercurization. Typically, the purified product is prepared within 30 minutes. The resin will remove free mercury contamination.

In another preferred embodiment of the invention, the preparation of the radiolabeled pyrimidine nucleoside or nucleotide entails contacting a radioactive ion (iodide, bromide or astatide) with a solution of recrystallized halomercuri-pyrimidine analog (preferably, about 1 mg/mL water), such as 5-chloromercuri-2'-deoxyuridine, in a centrifuge tube coated with an oxidizing agent (FIG. 1). The reaction to produce radiolabeled pyrimidine nucleoside or nucleotide occurs instantaneously. The resulting radiolabeled nucleoside or nucleotide contains no detectable UV-absorbing species, has insignificant mercury levels and is typically available for clinical applications within 5 minutes.

In a further embodiment, the present invention provides a kit for the production of radiolabeled nucleosides or nucleotides. The kit comprises a premeasured amount of recrystallized mercuri precursor such as for example, 5-chloromercuri-2'-deoxyuridine, and an oxidant in a sterilized container. In a preferred embodiment, the recrystallized precursor, e.g., ClHgUdR, is complexed with a carrier molecule, e.g., bound to the surface of beads or a test tube. In another embodiment, the surface of the beads or the walls of the test tube are also coated with the oxidant material. In another preferred embodiment, recrystallized ClHgUdR in solution is placed in a test tube, the wall of which is coated with an oxidant. Such kits are particularly useful for clinical applications.

The invention will be described in detail by exemplification using 2'-deoxyuridine. However, those skilled in the art will readily appreciate that the methods are equally useful for other nucleosides and nucleotides.

DETAILED DESCRIPTION OF THE INVENTION

Figure 1:
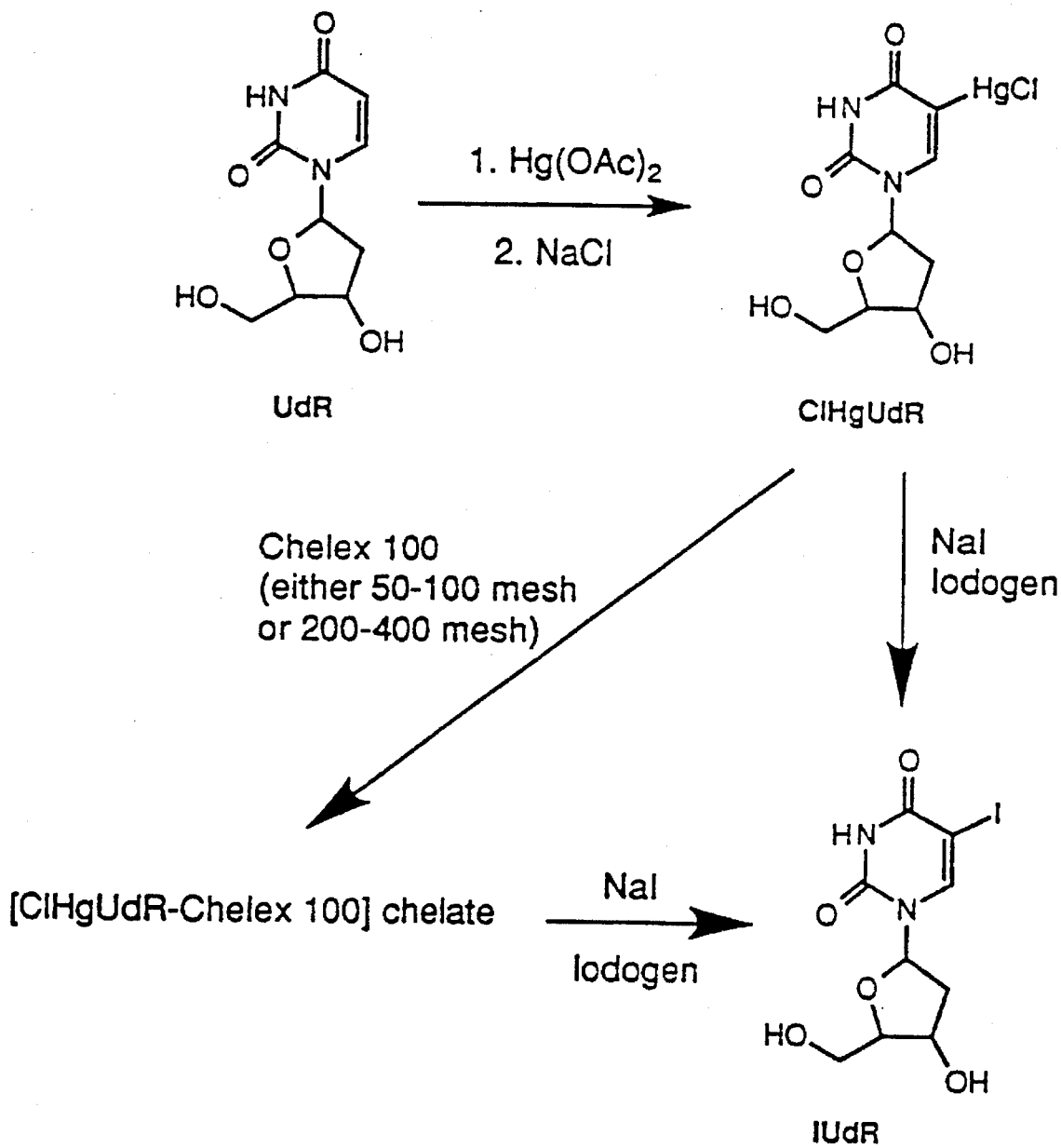
FIG. 1 shows the synthetic routes for preparation of radioiodinated IUdR.

Previously known methods for the synthesis of radiolabeled pyrimidine nucleosides, such as IUdR, typically are limited by long preparation times, low yield, and contaminating UV species. The method of this invention provides a method of making a radiolabeled pyrimidine nucleoside or nucleotide which comprises contacting a recrystallized halomercuri pyrimidine nucleoside or nucleotide with an oxidizing agent and dissolved radioactive ion whereby the water-soluble radioactive pyrimidine nucleoside or nucleotide is formed in solution. Preferred methods in accord with this invention typically produce products within about 5 minutes in quantitative yield and do not require a purification step (See Table 1).

TABLE 1

| | Comparison of methods for preparation of radiolabeled IUdR | | | | | | |
|---|---|---|---|---|---|---|---|
| | | | | Presence of UV-absorbing species[d] | | | Metal content[e] |
| Precursor | Time[a] | RY[b] | OY[c] | UdR | ClUdR | Unknown | (ppm) |
| Suspension ClHgUdR (4 mg) in water[f] | 6 h | ≧95 | 51 | + | + | − | 2.5 |
| ClHgUdR-Chelex 100 | 15 min | 55–60 | 30 | − | − | − | 0.1 |
| Aqueous solution ClHgUdR (10 μg) | 5 min | ≧95 | 95 | − | − | − | 1.7 |

[a]Total preparation period.
[b]Percent radiolabeling yield established by HPLC after radiosynthesis.
[c]Percent overall yield.
[d]$R_f$ of UdR, ClUdR and unknown = 5 min, 6 min, and 8 min, respectively.
[e]Established after final purification (in distilled water; [Hg] <0.050 ppm).
[f]Data from Kassis and Baranowska-Kortylewicz, U.S. Pat. No. 4,891,520 and Baranowska-Kortylewicz, et al. (1988)

In previous procedures, for example, a metallic precursor is prepared by the action of mercuric acetate on 2'-deoxyuridine (UdR). The white solid is treated with a sodium chloride solution and filtered (Kassis and Baranowska- Kortylewicz, U.S. Pat. No. 4,851,520; Baranowska-Kortylewicz, J., et al, 1988 supra). This water insoluble precursor is then used for iodination or radioiodination (Kassis and Baranowska-Kortylewicz, U.S. Pat. No. 4,851,520; Baranowska-Kortylewicz, J., et al, 1988, supra) or astatination (Visser, G. W. M., et al., (1980) *J. Labelled Cmpd. Radiopharm.* 18: 799–807).

For the present invention, an excess of solid sodium chloride is added to a suspension of the mercurial precursor composition while the mixture is still at 50° C. The solution becomes clear instantly, any residual solid is then filtered off, and the filtrate is kept in the refrigerator for recrystallization. Overnight, the metallic precursor forms needle-like crystals. This recrystallized form of the mercuri derivative, which unexpectedly was found to be water soluble, is then used for the preparation of the radiolabeled pyrimidine nucleoside or nucleotide, such as $^{125}$IUdR, $^{77}$BrUdR, or $^{211}$AtUdR.

Preferably, the water soluble mercuri derivative is immobilized on a solid surface prior to preparation of the radiolabeled nucleoside or nucleotide. In one embodiment of the invention, the water soluble mercuri derivative is adsorbed on an ion exchange resin or membrane prior to the preparation of the radiolabeled pyrimidine nucleoside or nucleotide. In another embodiment, the mercuri derivative is attached to a glass wall of a container or to glass beads by methods well known to those skilled in the art.

Typically, the recrystallized mercuri derivative is dissolved in water (e.g., $\geq 1$ mg/ml for ClHgUdR) for use in preparation of the radiolabeled pyrimidine nucleoside or nucleotide.

The methods of the present invention can be applied to any halomercuri-pyrimidine nucleoside such as 5-chloromercuri cytidine, 5-chloromercuri-2'-deoxycytidine, 5-chloromercuri uridine, 5-chloromercuri-2'-deoxyuridine, or to any halomercuri-pyrimidine nucleotide such as 5-chloromercuri-cytidine-5-mono-, di, or tri-phosphate, 5-chloromercuri-uridine-5'-mono-, di-, or tri-phosphate, or 5-chloromercuri-2'-deoxyuridine-5'-mono-, di-, or tri-phosphate. The corresponding 5-fluoromercuri compounds, and the like, can also be used.

For the purposes of illustration, the 5-chloromercuri-2'-deoxyuridine nucleoside will be referred to in detail as an example to demonstrate the present invention. It should be understood, however, that such reference does not limit the invention described herein to this nucleoside.

For the radiolabel, a radioactive iodine, bromine, chlorine or astatine ion can be employed in the form of any water-soluble salt, e.g., an alkali metal salt such as the sodium salt of a radioactive halide, for example, $^{123}$I, $^{124}$I, $^{125}$I, $^{126}$I, $^{128}$I, $^{129}$I, $^{130}$I, $^{131}$I, $^{132}$I, $^{133}$I, $^{134}$I, $^{135}$I, $^{74}$Br, $^{75}$Br, $^{76}$Br, $^{77}$Br, $^{80m}$Br, $^{82m}$Br, $^{83}$Br, $^{84}$Br, $^{34m}$Cl, $^{38}$Cl, $^{38m}$Cl, $^{39}$Cl or $^{211}$At, Preferably in carrier-free form. The concentration of iodide, bromide, chloride or astatide ion in the aqueous reaction medium can range from 0.1 mCi/mL to 1000 mCi/mL, preferably from 0.1 mCi/mL to 100 mCi/mL.

The oxidizing agent can be selected from a variety of oxidizing agents such as, for example, Chloramine T, nitric acid, N-chloro-succinimide, hydrogen peroxide or Iodogen. The oxidizing agent can be either water-soluble or water-insoluble, as in the case of Iodogen (1,3,4,6-tetrachloro-3α, 6α-diphenylglycouril). Preferably, a water insoluble oxidant is used to enable its rapid separation from the water soluble radiolabeled nucleoside or nucleotide.

Figure 5:
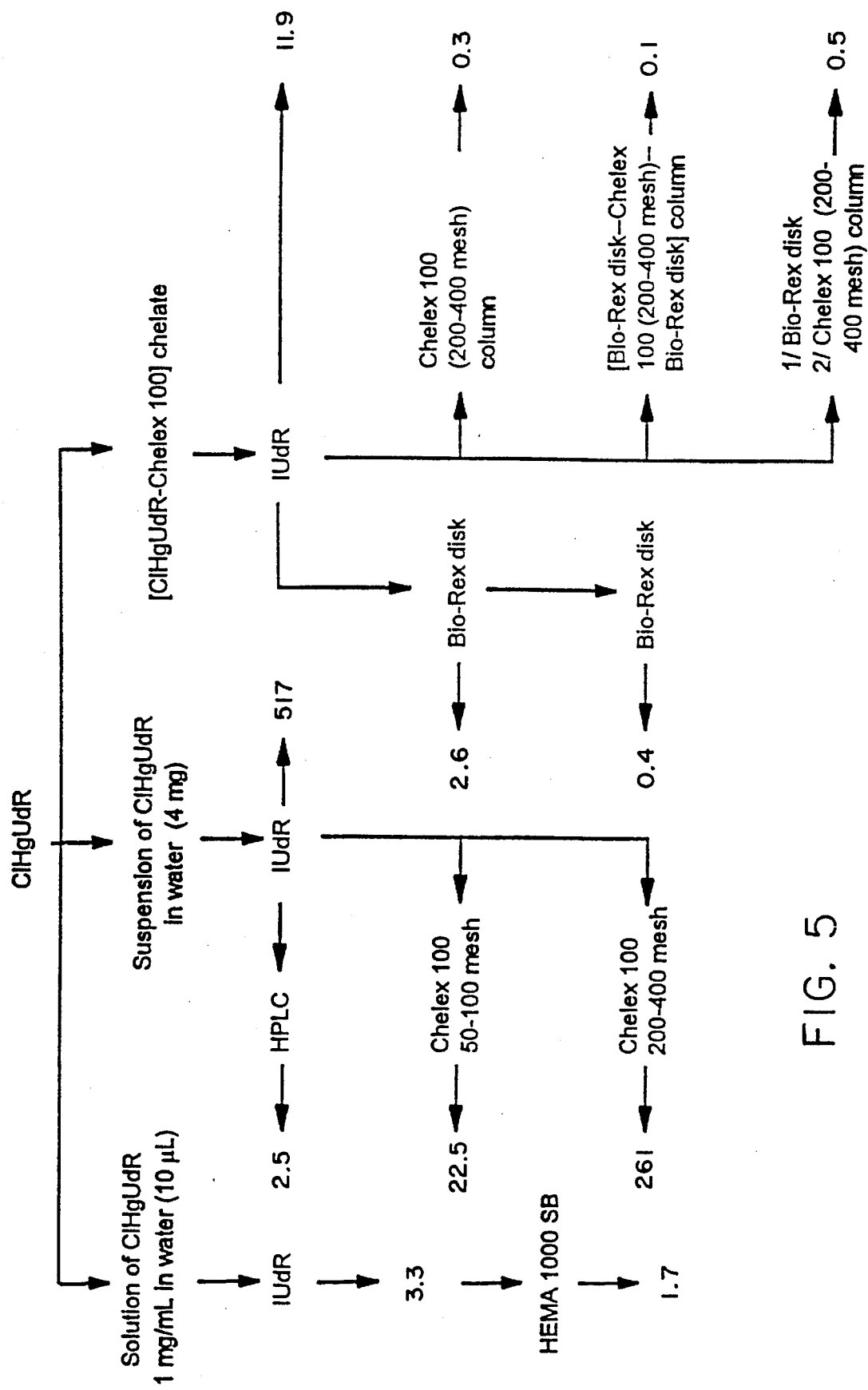
FIG. 5 shows the mercury content of radiolabeled IUdR synthesized from various ClHgUdR preparations before and after purification by different methods.

In one embodiment of the present invention, preparation time can be further reduced by chelation of the chloromercuri precursor to a cationic exchange resin, such as Chelex 100 (200–400 mesh) or the like (FIG. 1). Cationic exchange resins useful in the practice of the present invention can contain active groups such as carboxymethyl, sulphobutyl, sulfonic acid, carboxylate, and iminodiacetic acid groups, and the like. Such cation exchange resins can be in the bulk form, and also as a membrane or disc, e.g., for use in combination with a bacterial filter. Mercury contaminants in radiolabeled nucleoside or nucleotide preparations are removed by using a cation exchange resin that chelates heavy metals (FIG. 5). Useful resins include Amberlite and Dowex (available from Sigma Chemicals), HEMA 1000CM and HEMA 1000SB (available from Alltech), and AG 50 W, AG MP 50, BioRex 70 and Chelex 100 (available from BioRad). Chelex 100 (having iminodiacetic acid as the active group) is presently preferred. It has been found that some highly acidic resins (Dowex 50W-2 and Dowex 50W-8) can lead to the degradation (e.g., demercurization, deiodination) of the nucleotide or nucleoside.

In accord with a preferred embodiment of the present invention, an IUdR solution, prepared by demercurization, is incubated with the cationic exchange resin, preferably Chelex 100, to decrease the mercury concentration (e.g., from 517 ppm to 261 ppm (for 200–400 mesh), or more preferably, to 22.5 ppm (for 50–100 mesh, see FIG. 5). More preferably, the ClHgUdR is chelated directly with the resin (FIG. 1). For example, Chelex 100 (200–400 mesh) is used in a ratio in the range of about 2000:1 to about 10:1 (w/w; resin/mercury) to chelate the mercury present in a sample of 5-chloromercuri-2'-deoxyuridine (Table 1). Most preferably, 100 mg Chelex 100 per 10 mg ClHgUdR is used, producing a higher yield of radiolabeled product. It has been found that synthesis of $^{125}$IUdR from the ClHgUdR-Chelex 100 complex, whatever the mesh size of the resin used, confirms that the metallic precursor has been trapped by the resin. This is contrary to previous disclosures using a similar strategy which demonstrated that 5-mercuriacetate-2'-deoxyuridine is not retained by Chelex 100 (Dale, R. M. K., (1975) *Biochemistry* 14: 2447-2457).

Figure 2:
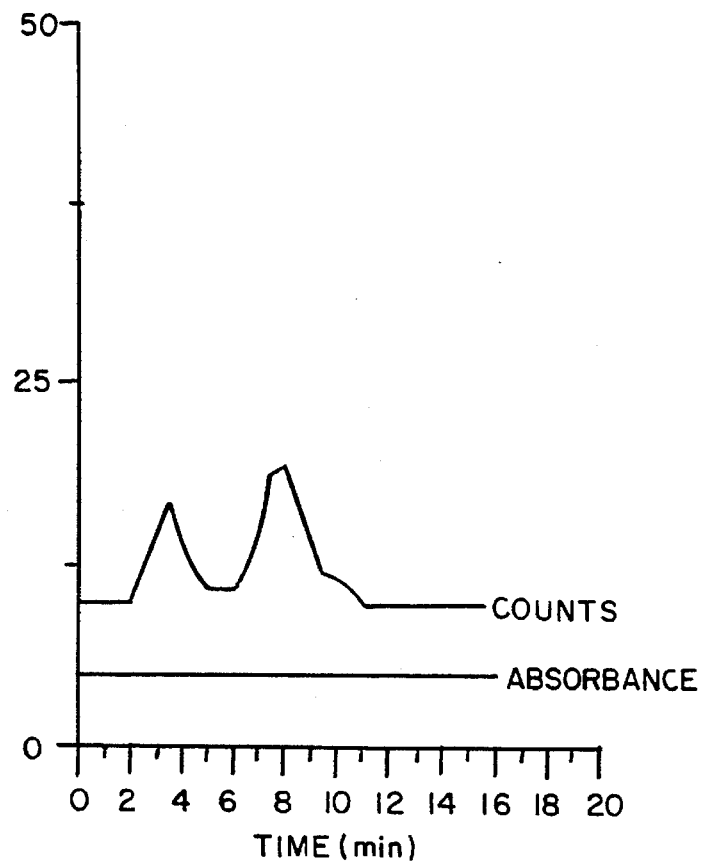
FIG. 2 is an HPLC chromatogram of [$^{125}$I] IUdR synthesized from ClHgUdR-Chelex 100 in the presence of the oxidant, Iodogen.

Once synthesized, the water soluble $^{125}$IUdR moves into the aqueous phase and is separated by centrifugation-filtration. As shown by chromatography, no "cold" impurities (e.g. UdR and ClUdR) are detected upon UV analysis (FIG. 2). When IUdR is synthesized from the ClHgUdR-Chelex 100 (200–400 mesh) complex, the mercury concentration of the sample decreases to 11.9 ppm (n=4) as determined by atomic absorption (FIG. 5). Extra elutions through Chelex 100 provides a concentration of mercury comparable with or lower than that observed after HPLC (2.5 ppm); 2.6 ppm after one elution through a Bio-Rex disc (Chelex 100 membrane); 0.5 ppm after elution through a Bio-Rex disc (Bio Rad, Hercules, Calif.) followed by elution through a Chelex 100 (200–400 mesh) column in a 5-mL syringe; 0.4 ppm after two successive elutions through Bio-Rex discs; 0.3 ppm after elution through Chelex 100 (200–400 mesh) set as a column in a 5-mL syringe; and 0.1 ppm after elution through a column in a 5-mL syringe consisting of Chelex 100 (200–400 mesh) with a Bio-Rex disc at each end. A quality radiolabeled IUdR can be produced with minimal mercury content and containing no UV-absorbing by-products.

Radiolabeled UdR, synthesized from the chelated complex is free of UV-absorbing by-products (FIG. 2) An extra elution through Chelex 100 (as a powder and/or as a membrane) decreases the concentration of mercury to a level lower than that obtained with HPLC purification (FIG. 5). This allows for the timely preparation of no-carrier-added, radiolabeled IUdR for biological or clinical use, typically within 30 minutes.

Figure 3:
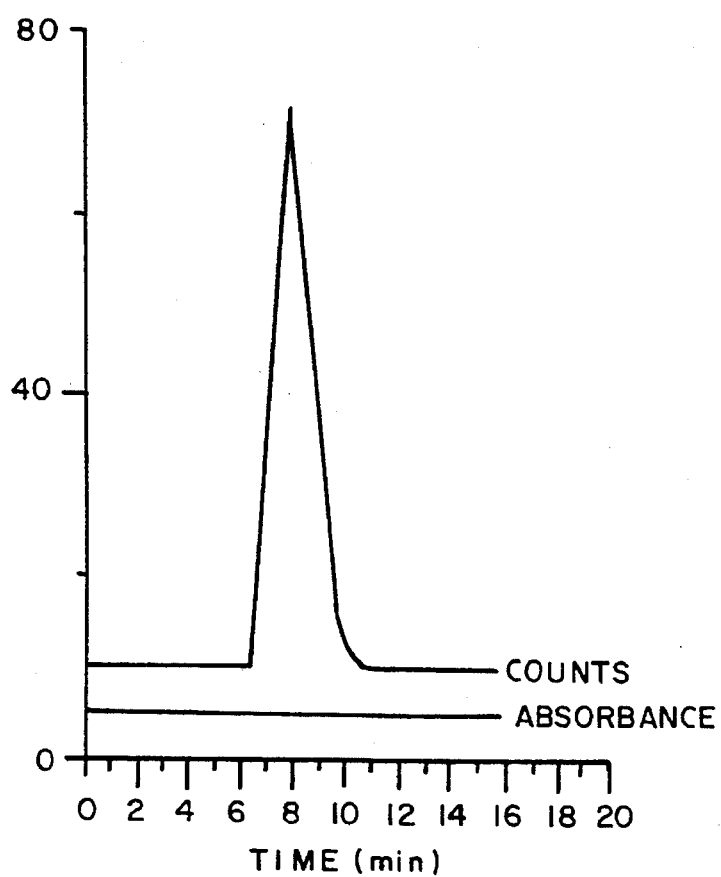
FIG. 3 is an HPLC chromatogram of [$^{125}$I] IUdR synthesized from an aqueous solution of ClHgUdR within an Iodogen-coated vial (15-sec incubation time).

In another preferred embodiment of this invention, the synthesis of radiolabeled IUdR from the mercuri precursor is instantaneous and does not require any purification (see FIG. 3 for HPLC profile). Although mercurial precursors, such as ClHgUdR, are known to be insoluble in numerous solvents, a solution of the recrystallized derivative (m.p. 230° C.) can be prepared at a concentration of about 1 mg/ml water (dissolution can be assisted by slight heating at 50° C.). The use of smaller amounts of dissolved ClHgUdR (0.1–10 μL of the solution), as opposed to 4 mg ClHgUdR in suspension as used in previously known procedures (Kassis and Baranowska-Kortylewicz, U.S. Pat. No. 4,821,520; Baranowska-Kortylewicz, J., et al. 1988, supra), minimizes the concentration of mercury in the final radiolabeled IUdR sample. For example, 10 μg of ClHgUdR (22 nmol) derivative is sufficient to synthesize approximately 5,300 mCi $^{123}$IUdR (specific activity 245,700 Ci/mmol), approximately 50 mCi $^{125}$IUdR (specific activity 2,200 Ci/mmol), and approximately 30 mCi $^{131}$IUdR (specific activity about 10 Ci/mg). The handling of such small volumes is eased by performing the radiolabeling in conical centrifuge tubes (200 μl), coated with the oxidizing agent, preferably Iodogen (10 μg/vial), and stored at 4° C. until needed.

Under these conditions, the radiolabeling is instantaneous (Table 1), and the final product does not need any further purification (FIG. 3). After sterilization, preferably through a 0.22-μm filter and a chelating disc (cation exchange resin membrane), the radiolabeled product is ready for biological or clinical use. The final labeled product is typically prepared in a maximum volume of 200 μL 0.9% sodium chloride within 5 minutes. Most importantly, the mercury content in the sample is lower than that obtained by previously known methods (Kassis and Baranowska-Kortylewicz, U.S. Pat. No. 4,821,520; Baranowska-Kortylewicz, J., et al. 1988, supra) that include HPLC purification (1.7 ppm versus 2.5 ppm, respectively; FIG. 5). Furthermore, HPLC chromatograms demonstrate that the quantitative transformation of sodium [$^{125}$I] iodine into $^{125}$IUdR and the absence of any by-products as monitored by UV (254 nm, sensitivity 0.05; FIG. 3).

Figure 4:
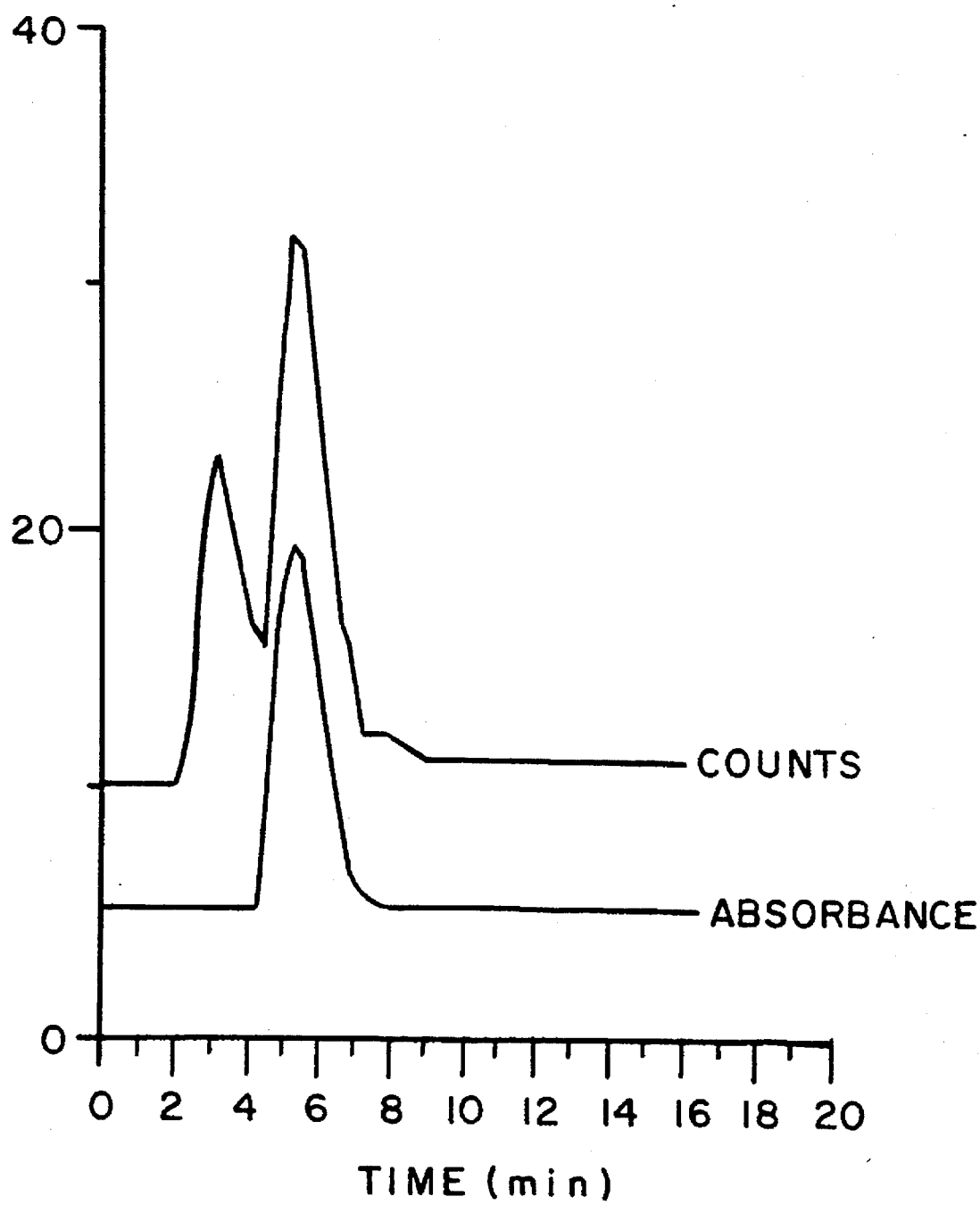
FIG. 4 is an HPLC chromatogram of reaction product from radioiodination of UdR within an Iodogen-coated vial (1 mg/mL in water).

To authenticate that the starting solution was ClHgUdR, the synthesis of IUdR was attempted starting with UdR (1 mg/mL in water) using the same conditions (10 μL UdR solution, 10 μg Iodogen and Na$^{125}$I). The results were similar to those reported by Bakker and Kaspersen (1981), the product of the reaction is 5-[$^{125}$I]iodo-6-hydroxy-2'-deoxyuridine which co-elutes with unreacted UdR on HPLC (FIG. 4).

Table 1 contains a comparison of the analysis of IUdR produced by the process of this invention and previously used procedures.

Because of the ease of the procedure and the rapid synthesis involved, the method of this invention is suitable for kit formulation. This invention provides for a kit in which the selected radionucleotide, e.g., $^{125}$IUdR, is prepared according to the method described herein and is contained in a pharmaceutically acceptable vehicle such as sterile normal saline yielding an effective diagnostic or therapeutic amount per dose unit. Generally speaking, each dose contains about 1–25 mCi (diagnosis) and 10–5000 mCi (therapy) of the selected radioactive compound. The pharmaceutically acceptable compositions for administration of the radiolabeled nucleoside or nucleotide can be formulated by methods known to those ordinarily skilled in pharmacology, using suitable non-toxic parenterally acceptable diluents such as normal saline, Ringer's solution, and formulating into sterile dosage forms for those administrations.

The water soluble recrystallized halomercuri compound of the present invention is preferably provided in easy to use kits that can be readily by the desired nuclear label. Such a kit, in accord with the present invention, comprises a sterilized, non-pyrogenic container containing the water-soluble halomercuri precursor compound, e.g., ClHgUdR. It is preferred that ClHgUdR be present in the container or test tube in aqueous solution in a concentration of about 1 mg/ml. Preferably, the container is a test tube, the wall of which is coated with a water insoluble oxidant. The kit may also contain a 0.22 μm filter, a chelating disc, 0.1 N HCl, and a syringe for the convenience of the user. Conveniently, an aqueous solution comprising 10 μl of ClHgUdR (1 mg/ml) and 10 μg Iodogen are provided in a sterilized, non-pyrogenic container in a kit for the preparation of radiolabeled UdR.

Preferably, the kit contains an apyrogenic sterilizing filter adjacent to an ion exchange membrane on which is immobilized a premeasured amount of a water soluble halomercuri pyrimidine nucleoside or nucleotide. More preferably, a water insoluble oxidizing agent is adjacent to the ion exchange membrane. The kit can be conveniently formed in a filter pack having the apyrogenic sterilizing filter, the ion exchange membrane and, optionally, the water insoluble oxidant stacked sequentially. A solution containing the radioactive label (and, optionally, a water soluble oxidant if a water insoluble oxidant is not in the pack) can be injected through the pack to form the radiolabeled nucleoside or nucleotide in a sterile form.

It is to be understood that the specific dose level and the particular dosage regimen for any particular patient will depend upon a variety of factors including for example, the age, body weight, sex and severity of the particular condition of the host undergoing therapy. The dosage regimen therefore needs to be individualized by the clinician based on clinical response.

The following specific examples are intended to illustrate more fully the nature of the invention without limiting its scope.

EXAMPLE 1

Preparation of 5-Chloromercuri-2'-deoxyuridine

A solution of mercuric acetate (1 mmol, 318.7 mg) and 2'-deoxyuridine (0.9 mmol, 205.6 mg) in 4 mL distilled water was stirred at 50° C. Within an hour, a white precipitate appeared and the heating was maintained for two additional hours. With continued stirring at 50° C., solid sodium chloride was added in small portions until the solution became clear; any residual precipitate was filtered off and the filtrate was refrigerated. A snowy white solid appeared overnight which was filtered and washed with water (25 mL) and ethanol (25 mL). After air-drying, ClHgUdR was obtained as white needle-like crystals (391.2 mg, 94%); mp: 230° C.; water soluble at 1 mg/ml. Elemental analysis of this water soluble compound determined:

Calculated: C=23.34 Found: 22.91

H=2.39 H=2.49

N=6.05 N=6.05

O=17.27 O=16.35

(Literature described nonrecrystallized ClHgUdR is reported to have mp: 210°–211° C. and is water insoluble— Kassis and Baranowska-Kortylewicz, U.S. Pat. No. 4,821,520; Baranowska-Kortylewicz, J., et al. 1988, supra.)

EXAMPLE 2

Chelation of 5-chloromercuri-2'-deoxyuridine with Chelex 100

The amount of Chelex 100 necessary to chelate all the mercury present in a sample of 5-chloromercuri-2'-deoxyuridine was established by incubating a constant quantity of the compound with increasing amounts of Chelex 100, either 50–100 mesh or 200–400 mesh (see Table 2). ClHgUdR (100 mg) was dissolved in a saturated sodium chloride solution (100 mL) and heated to 50° C. After cooling to room temperature, aliquots of the solution (2 mL) were incubated with 3,250 mg, 1,950 mg, 650 mg, 100 mg, 20 mg or 5 mg Chelex 100 (50–100 mesh) or 3,000 mg, 1,800 mg, 600 mg, 100 mg, 20 mg or 5 mg of Chelex 100 (200–400 mesh) for 30 min. Each sample was centrifuged for 3 min, and a 200μL aliquot of supernatant was submitted for mercury quantitation.

To prepare the ClHgUdR-Chelex 100 complex, 5-chloromercuri-2'-deoxyuridine (100 mg) was dissolved in a saturated sodium chloride solution (5 mL) and heated to 50° C. The solution was cooled to room temperature and 1 g Chelex 100 (50–100 mesh or 200–400 mesh) was added. The mixture was stirred for 30 minutes at room temperature, filtered, and washed consecutively with a saturated sodium chloride solution (100 mL) and water (100 mL). The ClHgUdR-Chelex 100 complex was air-dried overnight in preparation for iodination.

TABLE 2

Mercury content of aqueous phase after incubation of 2 mg ClHgUdR and various amounts of Chelex 100 in 2 mL 0.9% sodium chloride

| Chelex 50–100 mesh | | Chelex 200–400 mesh | |
|---|---|---|---|
| Quantity | [Hg] (ppm) | Quantity | [Hg] (ppm) |
| 3,250 mg | 0.073 | 3,000 mg | <0.050 |
| 1,950 mg | 0.26 | 1,800 mg | <0.050 |
| 650 mg | 0.32 | 600 mg | 0.16 |
| 100 mg | 2.54 | 100 mg | 1.14 |
| 20 mg | 3.37 | 20 mg | 3.39 |
| 5 mg | 4.17 | 5 mg | 3.61 |

EXAMPLE 3

Preparation of 5-Iodo- and 5-[$^{125}$I]iodo-2'-deoxyuridine from ClHgUdR-Chelex 100 complex In one vial of an Artkiss centrifugal filter unit (ArtChem Incorporated, Mountain View, Calif.), NaI (200 μL of 7.25 μg/mL distilled water) was added to a suspension of 10 mg 5-chloromercuri-2'-deoxyuridine-Chelex 100 (50–100 mesh or 200–400 mesh) and 10 mg Iodogen. The reaction was incubated at room temperature for 15 sec with occasional vortexing. The unit was inverted and centrifuged for 2 min. The sample was sent for mercury quantitation either without further processing or after filtration through a Bio-Rex disc (Chelex 100 membrane) and/or a Chelex 100 (200–400 mesh) column along with 500 μL distilled water to help in the elution.

For radioiodination in an Artkiss centrifugal filter unit, Na$^{125}$I(100–500 μCi) was added to a suspension of 10 mg 5-chloromercuri-2'-deoxyuridine-Chelex 100 (50–100 mesh or 200–400 mesh) and 10 mg Iodogen in distilled water (500 μL) containing 0.1 N HCl (10 μL). The reaction was incubated, centrifuged as above, and the filtrate was injected directly into the HPLC to determine the radiolabeling yield.

EXAMPLE 4

Preparation of 5-Iodo- and 5-[$^{125}$I]iodo-2'deoxyuridine from an aqueous solution of ClHgUdR 5-Chloromercuri-2'-deoxyuridine was dissolved (1 mg/mL distilled water) and filtered (0.45-μm HV4 Millipore filter). To 10 μL of this solution in a 1.6-mL or 200 μL conical centrifuge tube coated with 100 μg or 10 μg Iodogen, respectively, NaI (200 μL of 7.25 μg/mL distilled water) or Na$^{125}$I (0.1–2 mCi, 1–50 μL, pH 6) was added. The tube was vortexed for 15 sec and 100 μL water was added. In some studies, the solution was also centrifuged through HEMA 1000 SB resin followed by elution through a 0.22-μm apyrogenic sterilizing disc, which was rinsed with 100 μL 0.9% sodium chloride. In the case of IUdR, the amount of mercury was determined. In the case of $^{125}$IUdR, the radioactivity was measured and the overall yield was calculated.

The invention has been described in detail with particular reference to the preferred embodiments thereof. However, it will be appreciated that modifications and improvements within the spirit and scope of this invention may be made by those skilled in the art upon considering the present disclosure.

References

Bakker C. N. M. and Kaspersen F. M. (1981) The electrophilic iodination with $^{131}$I of $N_1$-substituted uracils using chloramine-T as oxidant. *Int. J. Appl. Radiat. Isot.* 32, 176–178.

Baranowska-Kortylewicz J., Helseth L. D., Lai J., Schneiderman M. H., Schneiderman G. S. and Dalrymple G. V. (1994) Radiolabeling kit/generator for 5-radiohalogenated uridines. *J. Labelled Cmpd. Radiopharm.* 34, 513–521.

Baranowska-Kortylewicz J., Makrigiorgos G. M., Van den Abbeele A. D., Berman R. M., Adelstein S. J. and Kassis A. I. (1991) 5[$^{123}$I]Iodo-2'-deoxyuridine in the radiotherapy of an early ascites tumor model. *Int. J. Radiat. Oncol. Biol. Phys.* 21, 1541–1551.

Baranowska-Kortylewicz J., Kinsey B. M., Layne W. W. and Kassis A. I. (1988) Radioiododemercuration: a simple synthesis of 5-[$^{123/125/127}$I]iodo-2'-deoxyuridine. *Appl. Radiat. Isot.* 39, 335–341.

Bloomer W. D. and Adelstein S. J. (1977) 5-$^{125}$I-iododeoxyuridine as prototype for radionuclide therapy with Auger emitters. *Nature* 265, 620–621.

Chan P. C., Lisco E. E., Lisco H. and Adelstein S. J. (1986) The radiotoxicity of iodine-125 in mammalian cells. II. A comparative study on cell survival and cytogenetic responses to $^{125}$IUdR, $^{131}$IUdR and $^3$HTdR. *Radiat. Res.* 67, 332–343.

Dale R. M. K., Martin E., Livingston D. C. and Ward D. C. (1975) Direct covalent mercuration of nucleotides and polynucleotides. *Biochemistry* 14, 2447–2457.

Dale R. M. K., Livingston D. C. and Ward D. C. (1973) The synthesis and enzymatic polymerization of nucleotides containing mercury: potential tools for nucleic acid sequencing and structural analysis. *Proc. Natl. Acad. Sci. USA* 70, 2238–2242.

Harrison K., Dalrymple G. V., Baranowska-Kortylewicz J., Schneiderman M. H., Holdeman K., Leichner P., Augustine S. C. and Jacobson D. (1994) Bladder cancer-[125I]IUdR imaging in preparation for [125I]IUdR therapy. *J. Nucl. Med.* 35, 144P.

Hofer K. G., Harris C. R. and Smith J. M. (1975) Radiotoxicity of intracellular $^{67}$Ga, $^{125}$I, and $^{3}$H. Nuclear versus cytoplasmic radiation effects in murine L1210 leukemia. *Int. J. Radiat. Biol.* 28, 225–241.

Kassis A. I., Sahu S. K., Wen P. Y. C., Nagel J. S., Black P. McL. and Adelstein S. J. (1994) Intrathecal $^{125}$IUdR in a rat model of meningeal carcinomatosis. *Proc. Am. Assoc. Cancer Res.* 35, 414.

Kassis A. I., Van den Abbeele A.D., Wen P. Y. C., Baranowska-Kortylewicz J., Metz K. R., Cook C., Sahu S. K., White J., Barclay P. D., Black P.M. and Adelstein S. J. (1993) 5-[I-$^{125}$]Iodo-2'-deoxyuridine in the radiotherapy of solid brain tumors in rats. *J. Nucl. Med.* 34, 241P.

Kassis A. I. (1990) 5-($^{123}$I/$^{125}$I)Iodo-2'-deoxyuridine for cancer diagnosis and therapy. *J. Nucl. Med. Allied Sci.* 34, 299–303.

Kassis A. I., Van den Abbeele A.D., Wen P. Y. C., Baranowska-Kortylewicz J., Aaronson R. A., DeSisto W. C., Lampson L. A., Black P. McL. and Adelstein S. J. (1990) Specific uptake of the Auger electron-emitting thymidine analogue 5-[$^{123}$I/$^{125}$I]iodo-2'-deoxyuridine in rat brain tumors: Diagnostic and therapeutic implications in humans. *Cancer Res.* 50, 5199–5203.

Kassis A. I., Fayad F., Kinsey B. M., Sastry K. S. R., Taube R. A. and Adelstein S. J. (1987) Radiotoxicity of $^{125}$I in mammalian cells. *Radiat. Res.* 111, 305–318.

Makrigiorgos G. M., Kassis A. I., Baranowska-Kortylewicz J., McElvany K. D., Welch M. J., Sastry K. S. R. and Adelstein S. J. (1989) Radiotoxicity of 5-[$^{125}$I]iodo-2'-deoxyuridine in V79 cells: a comparison with 5-[$^{125}$I]iodo-2'-deoxyuridine. *Radiat. Res.* 118, 532–544.

Mariani G., Di Sacco S., Volterrani D., Matteucci F., Baranowska-Kortylewicz J., Di Stefano R., Ricci S., Bellina C. R., Di Luca L., Buralli S., Falcone A., Salvadori P. A., Mosca F., Adelstein S. J. and Kassis A. I. (1994) Infusion of 5-[I-$^{125}$]-iodo-2'-deoxyuridine into the hepatic artery of patients with liver metastases from colorectal cancer. *J. Nucl. Med.* 35, 144P.

Mariani G., Cei A., Collecchi P., Baranowska-Kortylewicz J., Van den Abbeele A.D., Di Luca L., Di Stefano R., Viacava P., Ferdeghini E. M., Di Sacco S., Salvadori P. A., Bevilacqua G., Adelstein S. J., Mosca F. and Kassis A. I. (1993) Tumor targeting in vivo and metabolic fate of 5-[iodine-$^{125}$]iodo-2'-deoxyuridine following intratumoral injection in patients with colorectal cancer. *J. Nucl. Med.* 34, 1175–1183.

Tjuvajev J. G., Macapinlac H. A., Daghighian F., Scott A. M., Ginos J. Z., Finn R. D., Kothari P., Desai R., Zhang J., Beattie B., Graham M., Larson S. M. and Blasberg R. G. (1994) Imaging of brain tumor proliferative activity with iodine-123-iododeoxyuridine. *J. Nucl. Med.* 35, 1407–1417.

Van den Abbeele A. D., Baranowska-Kortylewicz J., Adelstein S. J., Carvalho P. A., Tutrone R. F., Richie J. P., Wen P. Y. C., Black P. McL., Mariani G. and Kassis A. I. (1992) Diagnostic and therapeutic applications of Auger-electron-emitting [$^{123}$I/$^{125}$I]iodo-2'-deoxyuridine in cancer. In *Biophysical Aspects of Auger Processes*, American Association of Physicists in Medicine Symposium Proceedings No 8 (Edited by Howell R. W., Narra V. R., Sastry K. S. R. and Rao D. V.) pp. 372–395. American Institute of Physics, Woodbury, N.Y.

Visser G. W. M., Diemer E. L. and Kaspersen F. M. (1980) The preparation of aromatic astatine compounds through aromatic mercury compounds Part II: astatination of pyrimidines and steroids. *J. Labelled Cmpd. Radiopharm.* 18, 799–807.

Wigerinck P., Kerremans L., Claes P., Snoeck R., Maugdal P., De Clercq E. and Herdewijn P. (1993) Synthesis and antiviral activity of 5-thien-2-yl-2'-deoxyuridine analogues. *J. Med. Chem.* 36, 538–543.

What is claimed is:

1. A method of making a radiolabeled pyrimidine nucleoside or nucleotide, the method comprising contacting in an aqueous solution (i) a radioactive iodide, bromide, chlorine or astatide ion and (ii) a water soluble halomercuri pyrimidine nucleoside or nucleotide with an oxidizing agent, whereby a water soluble pyrimidine nucleoside or nucleotide labeled with radioactive iodine, bromide, chlorine or astatine is formed.

2. The method as claimed in claim 1, wherein the water soluble halomercuri pyrimidine nucleoside or nucleotide is a 5-chloromercuri pyrimidine nucleoside or nucleotide.

3. The method as claimed in claim 2, wherein the water soluble halomercuri pyrimidine nucleoside is 5-chloromercuri-2'-deoxyuridine.

4. The method as claimed in claim 3, wherein the water soluble 5-chloromercuri-2'-deoxyuridine is present in a concentration of about 1 mg/ml.

5. The method as claimed in claim 2, wherein the water soluble halomercuri pyrimidine nucleoside is 5-chloromercuri-2'-deoxycytidine.

6. The method as claimed in claim 1, wherein the oxidizing agent is selected from the group consisting of Chloramine T, nitric acid, N-chloro-succinimide, hydrogen peroxide and Iodogen.

7. The method as claimed in claim 1, wherein the oxidizing agent is Iodogen.

8. The method as claimed in claim 1, wherein the oxidizing agent is hydrogen peroxide.

9. The method as claimed in claim 1, wherein the oxidizing agent is N-chloro-succinimide.

10. The method as claimed in claim 1, wherein the oxidizing agent is nitric acid.

11. The method as claimed in claim 1, wherein the oxidizing agent is Chloramine-T.

12. The method of claim 1 further comprising chelation of the water soluble halomercuri pyrimidine nucleoside or nucleotide to a cationic exchange resin.

13. The method of claim 1 further comprising chelation of the water soluble halomercuri pyrimidine nucleoside or nucleotide to a cationic exchange membrane.

14. The method of claim 1 further comprising immobilization of the water soluble halomercuri pyrimidine nucleoside or nucleotide is immobilized on a solid surface.

15. The method of claim 1 wherein a radioactive iodide ion is used to label the water soluble pyrimidine nucleoside or nucleotide.

16. The method of claim 1 wherein a radioactive bromide ion is used to label the water soluble pyrimidine nucleoside or nucleotide.

17. The method of claim 1 wherein a radioactive chloride ion is used to label the water soluble pyrimidine nucleoside or nucleotide.

18. The method of claim 1 wherein a radioactive astatide ion is used to label the water soluble pyrimidine nucleoside or nucleotide.

19. A kit comprising a predetermined amount of a water soluble halomercuri pyrimidine nucleoside or nucleotide in a sterile, non-pyrogenic container.

20. The kit of claim 19, further comprising an oxidant.

21. The kit of claim 19, further comprising a water insoluble oxidant coated on the wall of the container.

22. A kit suitable for forming a radiolabeled pyrimidine nucleoside or nucleotide, the kit comprising a premeasured amount of a water soluble chloromercuri pyrimidine nucleoside or nucleotide and an oxidizing agent in a sterile, non-pyrogenic container.

23. The kit of claim 22, containing water soluble 5-chloromercuri-2'-deoxyuridine.

24. The kit of claim 22, containing water soluble 5-chloromercuri-2'-deoxycytidine.

25. The kit of claim 22, further comprising chelation of the water soluble chloromercuri pyrimidine nucleoside or nucleotide to a cationic exchange resin.

26. The kit of claim 22, further comprising chelation of the water soluble chloromercuri pyrimidine nucleoside or nucleotide to a cationic exchange membrane.

27. The kit of claim 22, further comprising immobilization of the water soluble halomercuri pyrimidine nucleoside or nucleotide on a solid surface.

28. The kit of claim 22, wherein the solid surface is a glass surface.

29. The kit of claim 22, having water soluble 5-chloromercuri-2'-deoxyuridine in aqueous solution.

30. The kit of claim 29, wherein the water soluble 5-chloromercuri-2'-deoxyuridine is present in a concentration of about 1 mg/ml.

31. The kit of claim 22, further comprising casting of the container wall with a water insoluble oxidant.

32. The kit of in claim 22, wherein the oxidizing agent is selected from the group consisting of Chloramine T, nitric acid, N-chloro-succinimide, hydrogen peroxide and Iodogen.

33. The kit of claim 22, wherein the oxidizing agent is Iodogen.

34. The kit of claim 22, wherein the oxidizing agent is hydrogen peroxide.

35. The kit of claim 22, wherein the oxidizing agent is N-chloro-succinimide.

36. The kit of claim 22, wherein the oxidizing agent is nitric acid.

37. The kit of claim 22, wherein the oxidizing agent is Chloramine-T.

38. The kit of claim 22, wherein the oxidant is a water soluble oxidant.

39. The kit of claim 22, further comprising an apyrogenic, sterilizing filter and a chelating disc.

40. A kit suitable for forming a radiolabeled pyrimidine nucleoside or nucleotide, the kit comprising an apyrogenic sterilizing filter adjacent to an ion exchange membrane on which is immobilized a premeasured amount of a water soluble halomercuri pyrimidine nucleoside or nucleotide.

41. The kit of claim 40, containing water soluble 5-chloromercuri-2'-deoxyuridine.

42. The kit of claim 40, containing water soluble 5-chloromercuri-2'-deoxycytidine.

43. The kit of claim 45, wherein a water insoluble oxidizing agent is adjacent to the ion exchange membrane.

44. The kit of claim 43, wherein the water insoluble oxidizing agent is Iodogen.

45. Water soluble 5-chloromercuri-2'-deoxyuridine having a melting point of 230° C. and solubility in water of about 1 mg/ml.

* * * * *